United States Patent [19]

Kohayakawa et al.

[11] Patent Number: 5,031,623
[45] Date of Patent: Jul. 16, 1991

[54] NON-CONTACT TONOMETER

[75] Inventors: Yoshimi Kohayakawa, Yokohama; Shinya Tanaka, Tokyo, both of Japan

[73] Assignee: Canon Kabushiki Kaisha, Tokyo, Japan

[21] Appl. No.: 356,753

[22] Filed: May 25, 1989

[30] Foreign Application Priority Data

May 31, 1988 [JP] Japan .................. 63-133148
Sep. 22, 1988 [JP] Japan .................. 63-239450

[51] Int. Cl.⁵ .............................................. A61B 3/16
[52] U.S. Cl. ........................................ 128/648; 128/652
[58] Field of Search ............................. 128/645–652

[56] References Cited

U.S. PATENT DOCUMENTS

| 3,585,849 | 6/1971 | Grolman | 128/648 |
| 3,756,073 | 9/1973 | Lavallee et al. | 128/648 |
| 3,832,890 | 9/1974 | Grolman et al. | 128/648 |
| 4,580,559 | 4/1986 | L'Esperance | 128/645 |
| 4,724,843 | 2/1988 | Fisher | 128/648 |
| 4,817,620 | 4/1989 | Katsuragi et al. | 128/648 |
| 4,825,873 | 5/1989 | Kohayakawa | 128/648 |

FOREIGN PATENT DOCUMENTS 59-80228   5/1984 Japan .
60-83642   5/1985 Japan .
62-268524 11/1987 Japan .

Primary Examiner—Randall L. Green
Assistant Examiner—K. Reichle
Attorney, Agent, or Firm—Fitzpatrick, Cella, Harper & Scinto

[57] ABSTRACT

A non-contact tonometer includes plural sensor elements as a cornea deformation detecting system in a plane substantially conjugate with an illuminating light source through corneal reflection when the cornea of an eye to be examined is deformed by a predetermined amount, whereby measurement of the eye pressure is made possible even if the alignment of the apparatus relative to the eye to be examined is inaccurate.

7 Claims, 5 Drawing Sheets

NON-CONTACT TONOMETER

BACKGROUND OF THE INVENTION

1. Field of the Invention

This invention relates to a non-contact tonometer for blowing an air stream against the cornea of an eye to be examined to thereby deform the cornea, and optically detecting the deformation of the cornea to measure the eye pressure.

2. Related Background Art

In a tonometer of this type, whether the cornea-reflected light of a light beam for alignment detection travels in the direction of an air stream coaxial with the optic axis is photoelectrically detected. If the reflected light deviates from the optic axis or if the working distance deviates and the reflected light is not condensed on a photodetector, ejection of the air is stopped.

Referring to FIG. 1 of the accompanying drawings, E designates an eye to be examined, and Ec denotes the cornea thereof. A light beam for detecting the deformation of the shape of the cornea is projected as a parallel light beam from a light source 1 toward the cornea Ec of the eye E to be examined through a lens 2. The light reflected by the cornea is received through a lens 3 by a single photodetector 4 disposed on the optic axis and at the rearward focus position of the lens 3. On the other hand, a light beam for alignment detection is projected from a light source 5 onto the center of curvature of the cornea Ec via a lens 6, a beam splitter 7 and a lens 8, and when the cornea Ec is at a predetermined position, that is, when alignment is achieved, the light beam intactly returns along the same optical path, passes through the beam splitter 7 and a lens 9 and arrives at a photodetector 10. Also, compressed air provided by a cylinder mechanism comprising a cylinder 11 and a piston 12 is blown from a nozzle 13 disposed on the optic axis L toward the cornea Ec.

The direction of the air stream blown from the nozzle 13 toward the cornea Ec is coincident with the optic axis L, and when the cornea Ec is pressed flatly by this blown air, the light reception signal in the photodetector 4 becomes a maximum, and the eye pressure of the eye to be examined can be found from the air pressure at this point in time. The air pressure can be found from the output of a pressure sensor, not shown, which is provided in the cylinder 11.

Also, by the use of the cornea-reflected light of the light beam for alignment detection emitted from the light source 5, the alignment of the apparatus with the eye to be examined can be achieved because the output of the photodetector 10 rises when the cornea Ec is at a predetermined position. When there is misalignment, control means inhibits the measuring operation using the signal of the photodetector 10.

However, in the above-described example of the conventional art, the allowed alignment value is extremely narrow to ensure sufficient measurement accuracy, and much effort and time have been required for measurement and sufficient training has been necessary to accomplish efficient measurement.

The following factors are responsible for a measurement error caused by misalignment.

Firstly, part of the blown air stream escapes laterally and therefore, the amount of deformation of the cornea decreases and the eye pressure is measured to be too high. With regard to this, as shown in Japanese Laid-Open Patent Application No. 62-268524, the relation between misalignment and the apparent rise of the eye pressure is constant and this relation can be found in advance and corrected.

However, a measurement error occurs even for very slight misalignment. This occurs because the deformation of the cornea becomes asymmetrical due to the eccentricity of the blown air, and for example, the flatly pressed surface of the cornea inclines slightly from the perpendicular relative to the objective lens 8. In this case, the light beam for detection is condensed sideways from the light receiving element 4 disposed on the optic axis, and the predetermined deformation of the cornea cannot be accurately detected from the output of the light receiving element 4 and therefore a measurement error occurs.

Now, as another example of the prior art, there is one as shown in Japanese Laid-Open Patent Application No. 59-80228 wherein a sensor array is provided in the optical path of a cornea deformation detecting system and eye pressure is measured on the basis of the optical position of the cornea-reflected light on the sensor array. In this type of apparatus wherein such an optical position is found, the sensor array may basically be at any position in the direction of the optic axis relative to an eye to be examined, but in order that the optical position on the sensor array may be detected, the sensor array must be correctly aligned in a plane perpendicular to the optic axis relative to the eye to be examined. If measurement is effected in an inaccurate aligned state, the aforedescribed problem will likewise arise.

As a further example of the prior art, there is shown in Japanese Laid-Open Patent Application No. 60-83642 a tonometer in which the reflected light from the cornea of an eye to be examined is caused to enter three array sensors arranged in three meridian directions to thereby accomplish alignment, but this also is merely a tonometer of the type in which alignment is accurately effected before the measurement of eye pressure.

SUMMARY OF THE INVENTION

It is an object of the present invention to provide a tonometer which can optically correctly detect the predetermined deformation of the cornea of an eye to be examined and find the eye pressure of the eye to be examined even when an air stream is injected to the cornea of the eye to be examined in an inaccurately aligned state.

It is another object of the present invention to provide a tonometer which can correctly accomplish the measurement of eye pressure even if alignment is inaccurate and which is improved in operability.

It is still another object of the present invention to provide a novel tonometer in which the optical position is not detected by a sensor array but at the point in time at which the quantity of light reaches its peak is detected.

DESCRIPTION OF THE PREFERRED EMBODIMENTS

Figure 1:
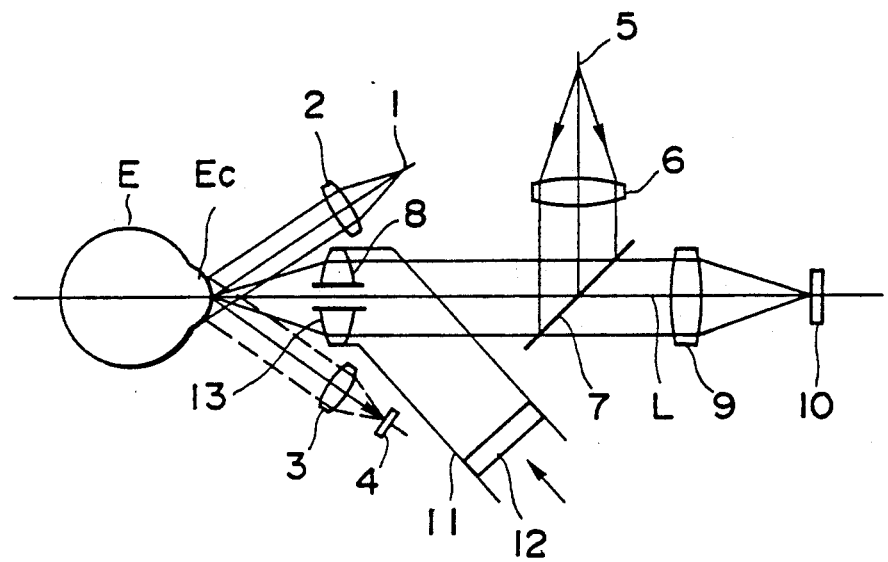
FIG. 1 illustrates an example of the prior art.
Figure 2:
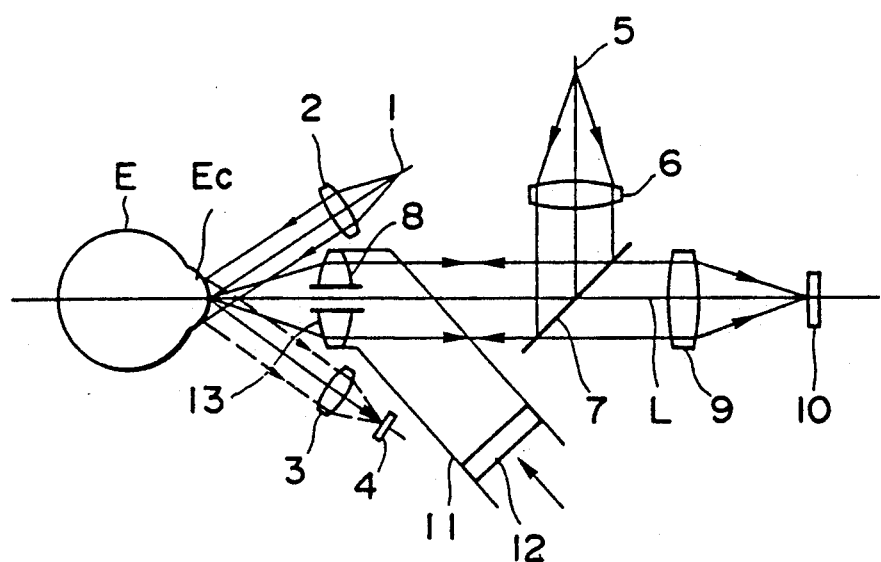
FIG. 2 shows the construction of an embodiment of the present invention.
Figure 3:
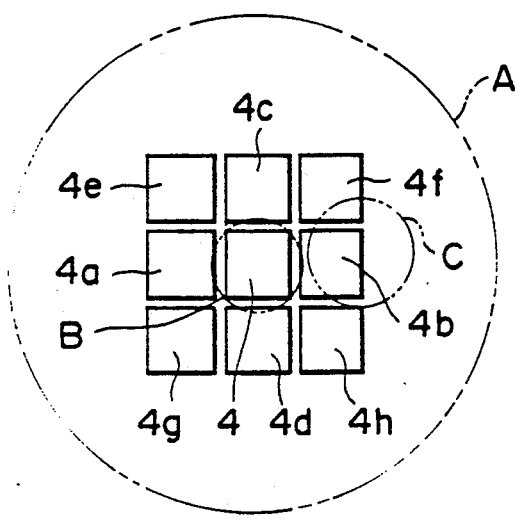
FIG. 3 shows the relation between a photodetector and the image of a light source.
Figure 4A:
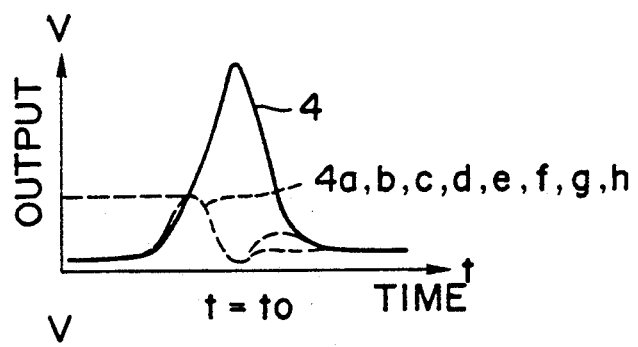
FIGS. 4A and 4B are graphs showing the variations in the outputs of light receiving elements during measurement.

Referring to FIG. 2 which shows the construction of an embodiment of the present invention, reference numerals similar to those in FIG. 1 designate similar members. The difference between this embodiment and the previously described example of the prior art is that light receiving elements $4a, \ldots, 4h$ are disposed in a parallel fashion near the light receiving element 4 of a light receiving optical system on a plane intersecting the optic axis, i.e. a plane conjugate with a light source 1 through corneal reflection when the cornea Ec is subjected to predetermined deformation (flatly pressed). FIG. 3 shows the arrangement of these plural sensor elements. Before the deformation of the cornea, a deformation detecting light beam emitted from the light source 1 is distributed on the surfaces of the light receiving elements while being widely spread to the outside of the light receiving elements $4, 4a, \ldots, 4h$ as shown, for example, by A in FIG. 3. When the air is blown against the cornea and the cornea assumes a predetermined deformed state, and alignment is correct, the light is condensed on the light receiving element 4 on the optic axis, as shown by B in FIG. 3. FIG. 4A shows the variation in the output of each light receiving element at this point in time. When the predetermined deformation of the cornea occurs at $t=t_0$, the output of the light receiving element 4 has a peak, but the detecting light beam does not arrive at the other light receiving elements $4a, \ldots, 4h$, which thus exhibit a variation in their outputs as indicated by the broken line.

Figure 4B:
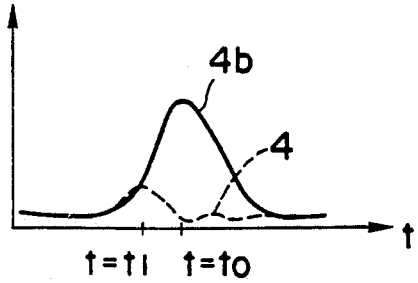

In contrast, when there is a very slight misalignment, asymmetrical deformation of the cornea occurs as previously described and the detecting light beam is condensed at a position deviated from the optic axis, as shown, for example, by C in FIG. 3. FIG. 4B shows the variations in the outputs of the light receiving elements 4 and 4b in such a case. In contrast with FIG. 4A, now at $t=t_0$ when the predetermined deformation of the cornea has occurred, the light receiving element 4b has a peak output, and the light receiving element 4 generates a lower peak at a different point of time $t=t_1$. Thus, in this case, to measure the correct eye pressure, the strength of the air stream can be known by the use of not the false peak generated in the light receiving element 4 at $t=t_1$, but the peak generated in the light receiving element 4b at $t=t_0$. That is, the strength of the air stream at the point of time at which the outputs of the light receiving elements $4a, \ldots, 4h$ can be known. The most reliable method therefor is to digitalize all the variations in the outputs of the light receiving elements $4, 4a, \ldots, 4h$ and the variation in the strength of the air stream, introduce them into the memory of a computer, compare and judge them after the completion of the measurement, select a true peak and convert the strength of the air stream corresponding to the point of time at which that peak is generated into an eye pressure value. The strength of the air stream can be obtained as by measuring the pressure in the cylinder by means of a pressure sensor, not shown.

The light receiving elements $4a, 4b, \ldots, 4h$ may be provided not only on substantially the same plane as the light receiving element 4, but also on a plane substantially conjugate with the light receiving element 4.

In the previous embodiment, there has been shown a method of introducing all the measurement outputs into a computer and effecting a calculation, whereas this method is reliable but complicated and expensive.

Figure 5:
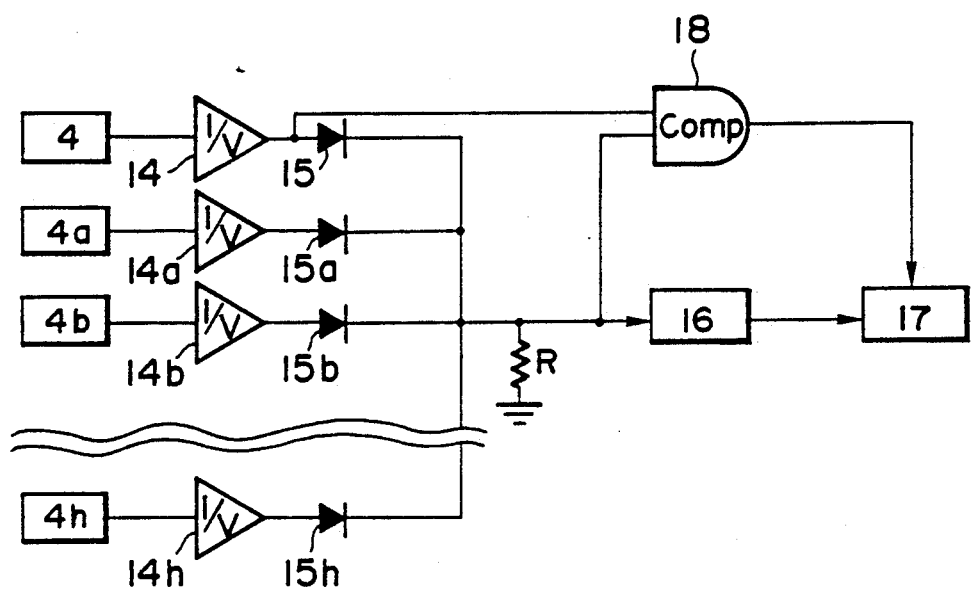
FIG. 5 diagrammatically shows a processing circuit in another embodiment.

Another embodiment of the present invention shown in FIG. 5 is a simplified form of the previous embodiment. In this embodiment, the outputs of the respective light receiving elements are I/V-converted by I/V (current-voltage) converters $14, 14a, \ldots, 14h$, whereafter an OR circuit is constituted by diodes $15, 15a, \ldots, 15h$ in an analogous fashion. This circuit utilizes the nature effect described with reference to FIG. 4 that the true peak has the greatest output, and only one of the diodes $15, 15a, \ldots, 15h$ to which the greatest signal is applied conducts in a forward direction and the signal thereof is input to a peak detecting circuit 16. The peak detecting circuit 16 sends a signal to a controller 17 at a point of time at which the peak of that input, i.e. the greatest one of the peaks of the outputs of the light receiving elements, is generated. In response to this signal, the controller 17 reads the strength of the air pressure from means such as an internal pressure sensor, not shown, which is mounted, for example, in the cylinder, and calculates the eye pressure of the eye to be examined therefrom. Also, a comparator 18 for comparing the output of the light receiving element 4 on the optic axis with the maximum peak value of the outputs of the diodes is provided, whereby it can be judged whether the detected greatest peak is that of the light receiving element 4 or other light receiving element. When by the use of the output of this comparator, the controller 17 judges that the greatest peak is not that from the light receiving element 4, there is carried out the process of warning the operator that there has been misalignment during measurement.

Figure 6:
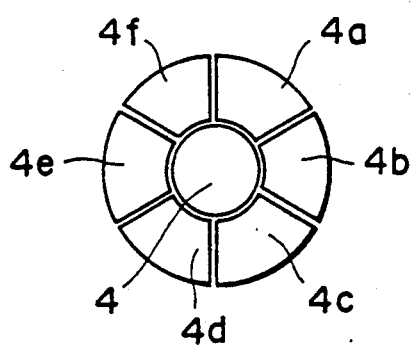
FIG. 6 shows a modification of the light receiving elements.

The arrangement of the light receiving elements is not limited to that shown in FIG. 3, but may be, for example, an annular arrangement around the element 4 on the optic axis as shown in FIG. 6.

Figure 7:
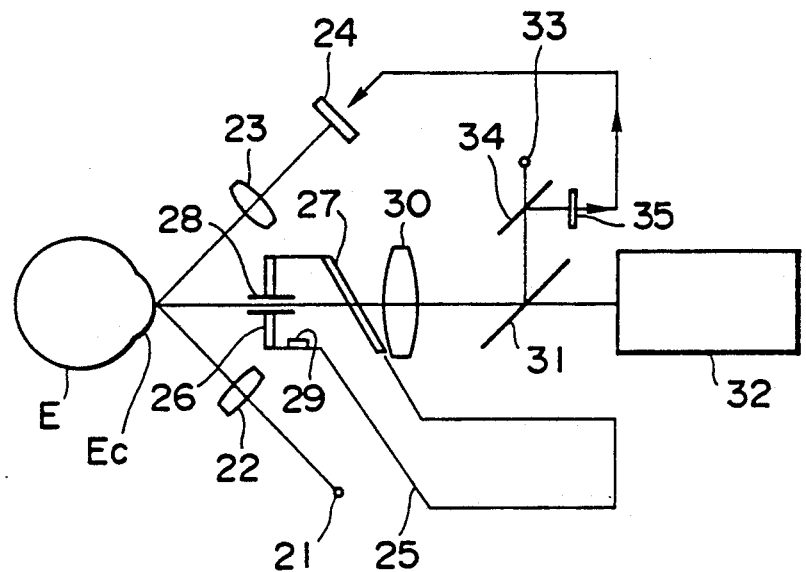
FIG. 7 shows the construction of still another embodiment.

FIG. 7 shows the construction of a further embodiment in which an optical system for detecting the deformation of the cornea Ec is provided to the side of the eye E to be examined and an air stream generating device is installed forwardly of the eye E to be examined. An index light source 21 comprising an LED or the like and a light projection lens 22 are disposed to the side of the cornea Ec, and a light receiving lens 23 and a sensor array 24 as plural sensor elements comprising a number of light receiving elements such as CCD's are disposed on the reflection side thereof. The index light source 21 and the sensor array 24 are installed at the focus positions, respectively, of the light projection lens 22 and the light receiving lens 23. A chamber 25 is disposed in front of the eye E to be examined and light-transmitting window portions 26 and 27 are provided before and behind the chamber 25, and in the central portion of the forward window portion 26, a nozzle 28 for air stream injection is installed toward the cornea Ec of the eye E to be examined. A pressure sensor 29 is installed in the chamber 25, and a lens 30, an obliquely disposed half-mirror 31 and a TV camera 32 are arranged in succession on the eye axis behind the chamber 25. A light source 33 for alignment and a half-mirror 34 are provided in the direction of reflection of the half-mirror 31, a position sensor 35 for alignment is installed in the direction of reflection of the half-mirror 34, and the alignment signal of the position sensor 35 is connected to the sensor array 24.

The air compressed in the chamber 25 by a piston is injected as an air stream from the nozzle 28 to the cornea Ec and deforms the cornea Ec. The light emitted from the index light source 21 is reflected by the cornea Ec and has its image projected onto the sensor array 24 by the light receiving lens 23. When the surface of the cornea is flattened by the air stream and the predetermined deformation of the cornea occurs, the index light source 21 becomes conjugate with the sensor array 24 through the reflection on the cornea Ec.

Figures 8A, 8B:
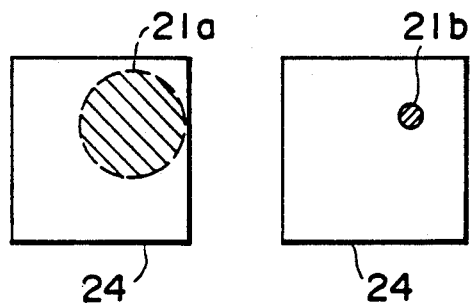
FIGS. 8A and 8B are front views of the cornea-reflected image on the light receiving element.

FIG. 8 shows the reflected image of the cornea Ec on the deformation detecting sensor array 24. FIG. 8A shows the reflected image 21a before the cornea Ec is deformed, and FIG. 8B shows the reflected image 21b when the cornea is pressed flatly and the index light source 21 becomes conjugate with the sensor array 24. The image is blurred and the light is diffused over a wide area before the deformation of the cornea, and the light becomes a small spot when the cornea is pressed flatly. The pressure when the light becomes such a small spot is measured by the pressure sensor 29, whereby the eye pressure value can be found.

It is because the alignment of the apparatus is not sufficiently achieved that, as shown in FIG. 8, the reflected image 21a deviates from the central portion of the sensor array 24. So, the position sensor 35 detects the deviation between the apparatus and the eye E to be examined in advance before the air stream is injected, and the reflected image from the cornea Ec is transmitted to the central portion of sensor array 24. By the utilization of the peak output of that sensor element on the sensor array 24 which is positioned at the center of the reflected image 21a, 21b, the deformation of the cornea Ec is detected.

Figure 9:
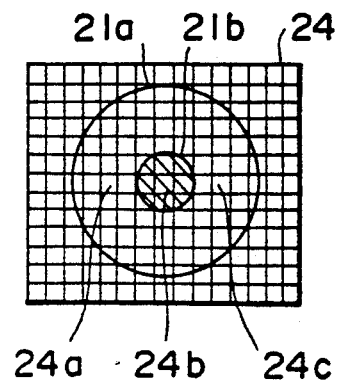
FIG. 9 is a front view of a sensor array.
Figure 10:
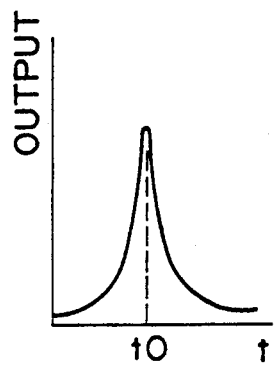
FIG. 10 is a graph showing the output characteristic of the sensor array.

As shown in FIG. 9, the sensor array 24 comprises a number of light receiving elements which are sensor elements, and assuming that the element 24b is positioned at the center of the reflected image 21a, 21b, the output of the element 24b corresponding to the air stream injection time is such as shown in FIG. 10. Here, at time t0 corresponding to the peak in FIG. 10, the index light source 21 and the sensor array 24 become conjugate with each other, and it is detected that the cornea Ec has been subjected to the predetermined deformation.

If as shown in FIG. 9, the output of the central element 24b is Sb and the outputs of the marginal elements 24a and 24c are Sa and Sc, respectively, when the reflected image 21a is blurred, the reflected light enters the marginal elements 24a and 24c as well, but when the cornea Ec is pressed flatly and the reflected image 21b becomes small, no light is applied to the marginal elements 24a and 24c. So, if the ratio of the output of the central element to the sum of the outputs of the marginal elements, i.e. Sb/(Sa+Sc), is calculated, the peak at the time t0 will become sharper and detection accuracy will be enhanced.

Figure 11:
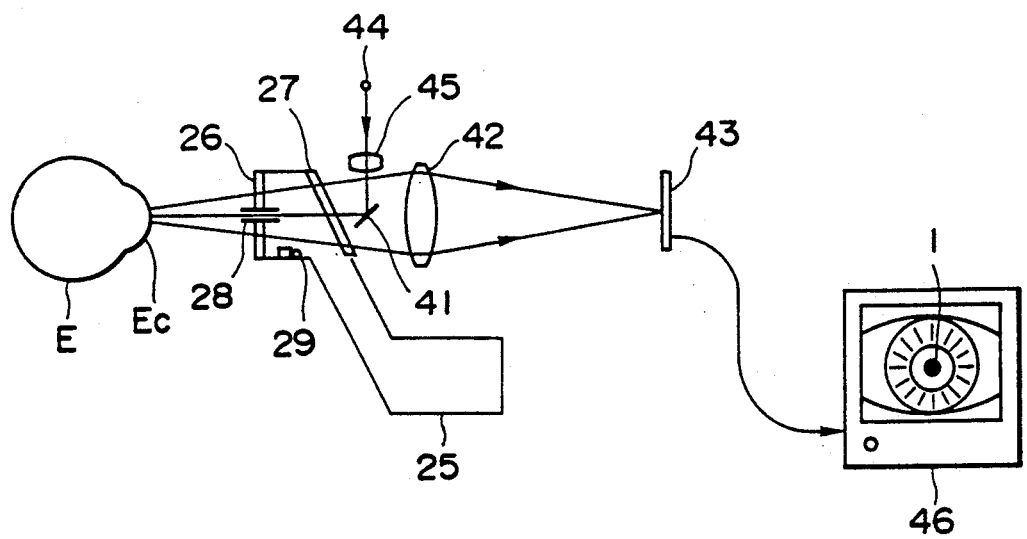
FIG. 11 shows the construction of yet still another embodiment.

FIG. 11 shows still another embodiment, in which reference numerals similar to those in FIG. 7 designate similar members. An air stream injection device similar to that shown in the embodiment of FIG. 7 is provided forwardly of the eye E to be examined, and a small mirror 41, a light receiving lens 42 and a sensor array 43 such as a CCD are arranged in succession rearwardly of the window portion 27, and a light source 44 for index and alignment such as an LED and a light projection lens 45 are provided in the direction of reflection of the small mirror 41. The sensor array 43 is used as an image sensor, and the output of the sensor array is connected to a TV monitor 46 on which the reflected image is displayed. The cornea-reflected image I of the light source 44 becomes more clear-cut as the air stream is injected and the cornea Ec is deformed. To detect the predetermined deformation of the cornea, the ratio of the output of the central element of the reflected image I on the sensor array 43 to the sum of the outputs of the marginal elements can be calculated and the point of time at which that ratio exceeds a predetermined value in the vicinity of the peak can be detected. The eye pressure value can be measured from the air pressure of the injected air stream at that point in time.

We claim:

1. A non-contact tonometer, comprising:
   air stream generating means for generating and transmitting an air stream to the cornea of an eye to be examined to thereby deform the cornea by a predetermined amount;
   light applying means, having an illuminating light source, for applying a light to the cornea of the eye to be examined to detect the deformation of the cornea;
   a light receiving optical system, having a condensing lens for receiving the applied light reflected from the cornea of the eye to be examined;
   plural sensor means provided in the path of said light receiving optical system for detecting the quantity of reflected light from the cornea of the eye to be examined, each of said plural sensor means being disposed to receive focused light reflected from the cornea when the cornea of the eye to be examined is deformed by a predetermined amount and to receive unfocused light reflected from the cornea when the cornea of the eye to be examined is in a normal, undeformed state; and
   means for calculating the eye pressure when the cornea of the eye to be examined is deformed by said predetermined amount at least by the use of an output of one of said plural sensor means whose light reception output is greatest.

2. A non-contact tonometer according to claim 1, wherein the ratio of the output (Sb) of said one sensor means to the sum (Sa+Sc) of the outputs of the sensor means around said one sensor means is calculated by said means for calculating the eye pressure.

3. A non-contact tonometer according to claim 2, wherein said air stream generating means is provided with a pressure sensor, and the eye pressure is calculated by said means for calculating from the pressure of said pressure sensor when the cornea of the eye to be examined is deformed by said predetermined amount.

4. A non-contact tonometer according to claim 2, wherein said plural sensor means are a sensor array.

5. A non-contact tonometer according to claim 4 further comprising detecting means for detecting the status of alignment of said tonometer before the stream is generated, wherein the position of the reflected light on said sensor array when the cornea of the eye to be examined is deformed by a predetermined amount is determined on the basis of the output of said detecting means.

6. A non-contact tonometer according to claim 1, wherein said air stream generating means is provided with a pressure sensor, and the eye pressure is calculated by said means for calculating from the pressure of said pressure sensor when the cornea of the eye to be examined is deformed by said predetermined amount.

7. A non-contact tonometer according to claim 1, wherein said plural sensor means are provided with a light receiving element disposed on a optic axis of said light receiving optical system, and light receiving elements disposed around said light receiving element as viewed in the direction of said optic axis.

* * * * *

UNITED STATES PATENT AND TRADEMARK OFFICE
CERTIFICATE OF CORRECTION

PATENT NO. : 5,031,623

DATED : July 16, 1991

INVENTOR(S) : KOHAYAKAWA ET AL.

It is certified that error appears in the above-identified patent and that said Letters Patent is hereby corrected as shown below:

COLUMN 3

Line 15, "still" should be deleted;
Line 28, "i.e." should read --i.e.,--; and

COLUMN 4

Line 25, "nature" should be deleted.

COLUMN 7

Line 1, "claim 4" should read --claim 4,--.

COLUMN 8

Line 6, "a" should read --an--.

Signed and Sealed this

Sixteenth Day of March, 1993

Attest:

STEPHEN G. KUNIN

Attesting Officer

Acting Commissioner of Patents and Trademarks